United States Patent
Martin et al.

(10) Patent No.: US 11,141,193 B1
(45) Date of Patent: Oct. 12, 2021

(54) INCISING TOOL FOR EASING CHILDBIRTH AND IMPROVING MATERNAL HEALING AND METHOD OF ITS USE

(71) Applicants: William Clayton Martin, Stillwater, OK (US); Corby Wade Smithton, Stillwater, OK (US)

(72) Inventors: William Clayton Martin, Stillwater, OK (US); Corby Wade Smithton, Stillwater, OK (US)

( * ) Notice: Subject to any disclaimer, the term of this patent is extended or adjusted under 35 U.S.C. 154(b) by 0 days.

(21) Appl. No.: 16/174,999

(22) Filed: Oct. 30, 2018

Related U.S. Application Data (60) Provisional application No. 62/578,863, filed on Oct. 30, 2017.

(51) Int. Cl.
*A61B 17/42* (2006.01)
*A61B 17/3209* (2006.01)
*A61B 17/00* (2006.01)

(52) U.S. Cl.
CPC .......... *A61B 17/42* (2013.01); *A61B 17/3209* (2013.01); *A61B 2017/00367* (2013.01)

(58) Field of Classification Search
CPC ................ A61B 17/42; A61B 17/3209; A61B 2017/00367; A61B 17/323093; A61B 17/3211; A61B 2017/00424; A61B 2017/00429; A61B 2090/0801; A61B 2090/08021; A61B 17/4208; A61B 2017/32093; A61B 2017/32096; A61B 2017/32113; A61B 2017/32116; A61B 17/3213; A61B 17/326
See application file for complete search history.

(56) References Cited

U.S. PATENT DOCUMENTS

| | | | | |
|---|---|---|---|---|
| 4,139,939 A | * | 2/1979 | Crooks | B26B 5/003 30/162 |
| 4,516,575 A | * | 5/1985 | Gerhard | A61F 9/0133 30/320 |
| 4,604,804 A | * | 8/1986 | Sparks | B26B 5/00 30/162 |
| 4,759,363 A | * | 7/1988 | Jensen | A61B 17/32093 30/293 |
| 5,211,652 A | * | 5/1993 | Derbyshire | A61B 17/3213 606/182 |
| 5,341,822 A | * | 8/1994 | Farr | A61F 15/02 128/898 |
| 5,370,654 A | * | 12/1994 | Abidin | A61B 17/3211 30/162 |
| 5,391,177 A | * | 2/1995 | Schwartz | A61B 17/3211 30/151 |

(Continued)

*Primary Examiner* — Jonathan G Riley
(74) *Attorney, Agent, or Firm* — GableGotwals (57) ABSTRACT

Embodiments of pelvic floor muscle incising tool of this disclosure include a housing that provides an effective way to shoe-horn the tool and its surgical cutting blade into a precise location between a baby's head and the mother's pelvic floor muscles. The housing provides a duckbill shape that allows for precise placement of the blade to create the incision, protects the baby from the cutting blade (creating only a posterior incision in the vaginal canal), distributes forces applied by and to the baby's head, and allows for concealed extraction of the blade after the incision has been made.

19 Claims, 5 Drawing Sheets

(56) References Cited

U.S. PATENT DOCUMENTS

| | | | | |
|---|---|---|---|---|
| 5,545,175 | A | * | 8/1996 | Abidin ............... A61B 17/3211 30/162 |
| 5,620,454 | A | * | 4/1997 | Pierce ................. A61B 17/32 30/162 |
| 5,730,751 | A | * | 3/1998 | Dillon ............... A61B 17/3211 606/167 |
| 5,749,886 | A | * | 5/1998 | Abidin ............... A61B 17/3211 30/162 |
| 6,623,499 | B1 | * | 9/2003 | Andreini ........... A61B 17/3211 30/329 |
| 7,306,615 | B2 | * | 12/2007 | Wilson ............... A61B 17/3211 30/151 |
| D788,303 | S | * | 5/2017 | Yurek ......................... D24/147 |
| 2007/0078472 | A1 | * | 4/2007 | Singh ................. A61B 17/3211 606/167 |
| 2007/0088374 | A1 | * | 4/2007 | Masury .............. A61B 17/3211 606/167 |
| 2010/0234865 | A1 | * | 9/2010 | Lafauci .............. A61B 17/3211 606/167 |
| 2011/0106123 | A1 | * | 5/2011 | Lafauci .............. A61B 17/3211 606/167 |
| 2014/0182140 | A1 | * | 7/2014 | Rosenhan ............... B26B 5/003 30/162 |
| 2018/0000508 | A1 | * | 1/2018 | Hu ..................... A61B 17/3211 |

\* cited by examiner

INCISING TOOL FOR EASING CHILDBIRTH
AND IMPROVING MATERNAL HEALING
AND METHOD OF ITS USE

CROSS-REFERENCE TO CO-PENDING
APPLICATION

This application claims priority to U.S. Provisional Application No. 62/578,863 filed Oct. 30, 2017.

BACKGROUND

Field of the Disclosure

This disclosure is in the field of medical apparatuses, systems, and methods used during child birth. More specifically, the disclosure relates to a tool for creating an incision(s) to relieve tension in the pelvic floor muscles during child birth.

Description of the Related Art

Current methods for the reduction of resistance in the vaginal canal to the baby's passage are the medio-lateral, median, lateral, and J-shaped episiotomies. Episiotomies are primarily used to enlarge the vaginal opening and usually performed with sterile scissors. The anterior and posterior of the vagina and surrounding tissue and muscle are generally incised.

SUMMARY

In embodiments of this disclosure, a surgical cutting blade is obscured such that an incising tool containing the cutting blade can be vaginally inserted to the local point of muscular and tissue tension that is causing resistance to a baby's passage through the birth canal and, subsequent to insertion, the cutting blade can be extended to create a cut that relieves the tension and allows for easier passage of the baby through the birth canal. The incision created by the tool reduces the muscle systems and tissue (both anterior and posterior) cut during standard episiotomies, thereby minimizing the damage done to the mother, improving subsequent healing, and minimizing the potential for other medical complications.

In some embodiments of the incising tool, the a #10 steel scalpel blade is used as the cutting blade. The cutting blade may be mounted onto a plunger inside of a protective housing and retained such that it is biased toward the actuator end of the plunger, requiring force on the plunger to express the blade through a blade expressing aperture of the housing. The housing has unique contours—including a curved section having a duckbill-shape—that allow for precise placement of the blade to create the incision, protects the child from the cutting blade (creating only a posterior incision in the vaginal canal), and allows for concealed extraction of the blade after the incision has been made. In embodiments, the incising tool is designed for ambidextrous, single-handed use.

The incising tool may comprise a housing including an insertion end, an actuator end, and an exterior wall surface located between the ends, the housing narrowing in height toward the insertion end from the actuator end, a portion of the exterior wall surface located toward the actuator end including a plurality of spaced-apart annular ribs, another portion of the exterior wall surface forming a curved section toward the insertion end, the curved section narrowing toward the insertion end and including a flat upper wall surface and a blade opening located opposite the flat top wall surface, the housing further containing a pair of alignment pins arranged transverse to a central longitudinal centerline of the housing. The flat upper wall surface may include a slight crown or draft angle for manufacturability purposes. A plunger housed by the housing may include a proximal end, a distal end, and a mount configured to retain a surgical blade located on the distal end, the proximal end of the plunger extending outward past the actuator end of the housing when in a fully retracted position, the plunger further including a retention pin and a pair alignment slots arranged parallel to the central longitudinal centerline of the housing and extending lengthwise, each of the alignment slots containing a respective alignment pin of the pair of alignment pins, the retention pin arranged transverse to a central longitudinal centerline of the plunger and coaxially aligned with one of the alignment slots. A surgical blade may be mounted on the mount.

The tool may further include biasing means such as an elastomeric band having one end retained by the retention pin and another end retained by one of the alignment pins of the housing. The elastomeric band biases the plunger (and therefore the surgical cutting blade) toward the actuator end for concealment within the housing. When the plunger is in the fully retracted position, the cutting blade resides entirely within the housing. Applying force to the plunger expresses at least a portion of the blade outside of the housing.

The housing may be a two-part housing comprising complementary shaped front (first) housing and rear (second) housing halves that are connectable to one another. (Note that depending on the viewer's orientation, the housing halves could be labeled as left and right halves.) In some embodiments one half includes a plurality of snap connectors and the other half includes a plurality of snap connector receivers. Each half may also include a plurality plunger guides located about an inner periphery of the housing, the plunger guides arranged transverse to the central longitudinal centerline of the housing. The plunger may narrow in height toward the distal end from the proximal end. The plunger may be I-shaped in cross section and include a central web with a flange located about a periphery of the web. A length of the alignment slots determines a total travel distance of the plunger between the fully retracted and fully extended positions.

In embodiments of a method of use, the incising tool may be inserted between the baby's head and the mother's pelvic floor. During insertion and placement, the surgical cutting blade is concealed in the housing as the housing's unique contour helps guide the blade into the desired position. The cutting blade may then be extended from concealment creating an incision in the mother's pelvic floor thereby creating a local relief in the muscular band impeding the baby's passage through the birth canal. The cutting blade may then be retracted into the housing for concealment.

ELEMENTS AND NUMBERING USED IN THE DRAWINGS AND DETAILED DESCRIPTION

Figure 1:
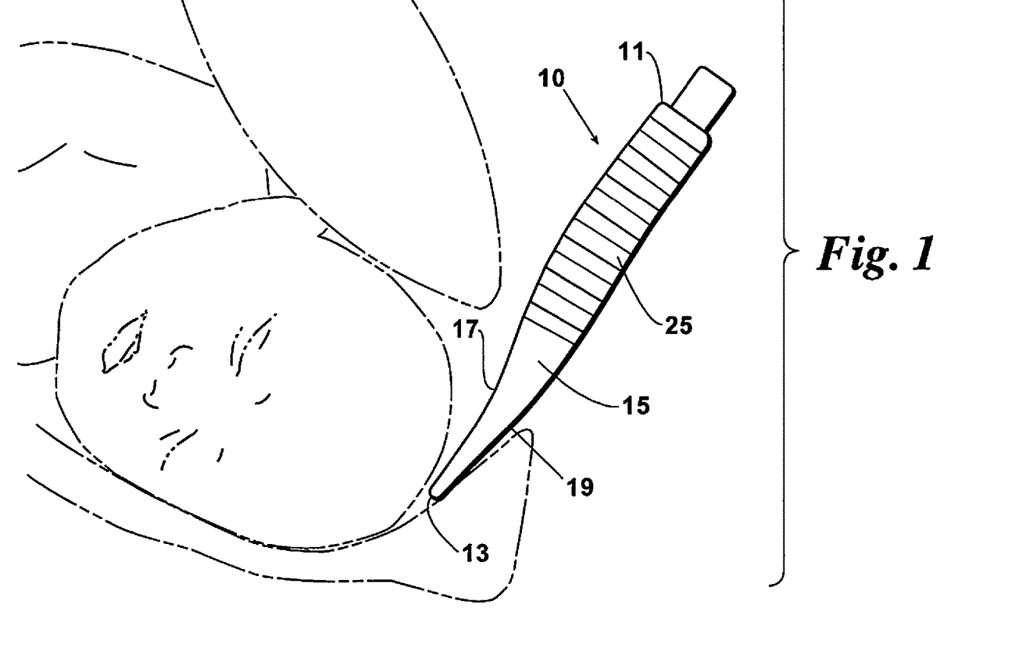
FIG. 1 is a view of an embodiment of an incising tool of this disclosure in position prior to insertion between the baby's head and the muscular ring under tension which is causing obstruction. The surgical cutting blade is in the retracted state.
Figure 2:
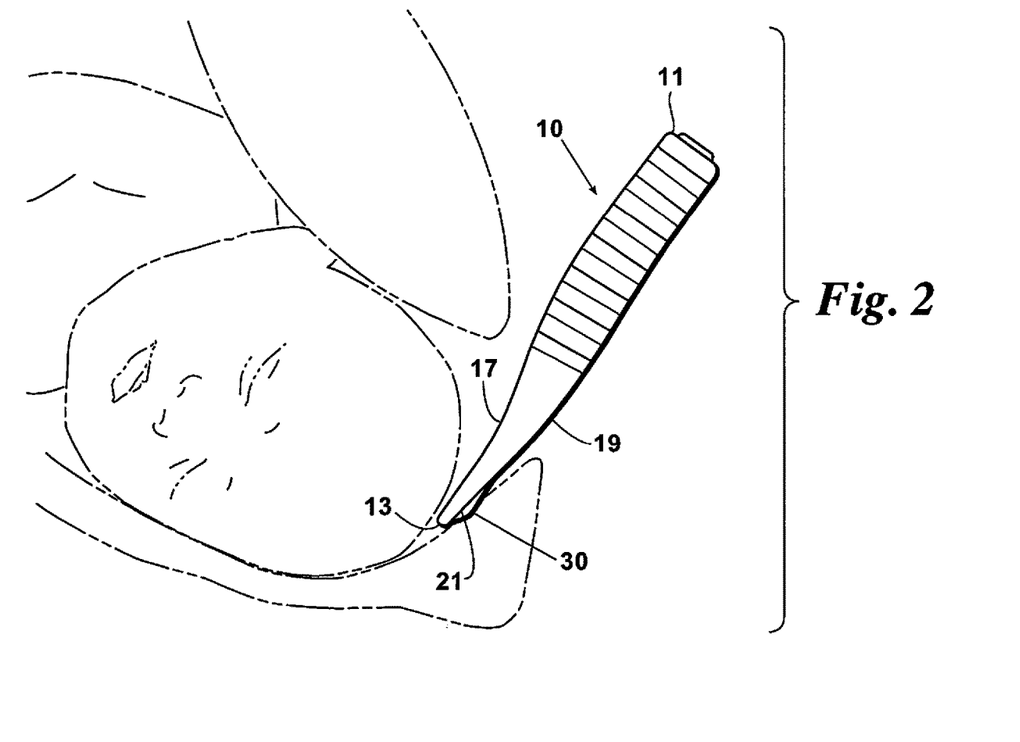
FIG. 2 is a view showing the incising tool of FIG. 1 inserted between the baby's head and the muscular ring causing obstruction. The cutting blade is in the extended or expressed state. When in the expressed state, the cutting blade remains rearward of the insertion end of the incising tool. During incising, the duckbill-shaped upper wall surface distributes forces applied by and to the baby's head.
Figures 3, 4:
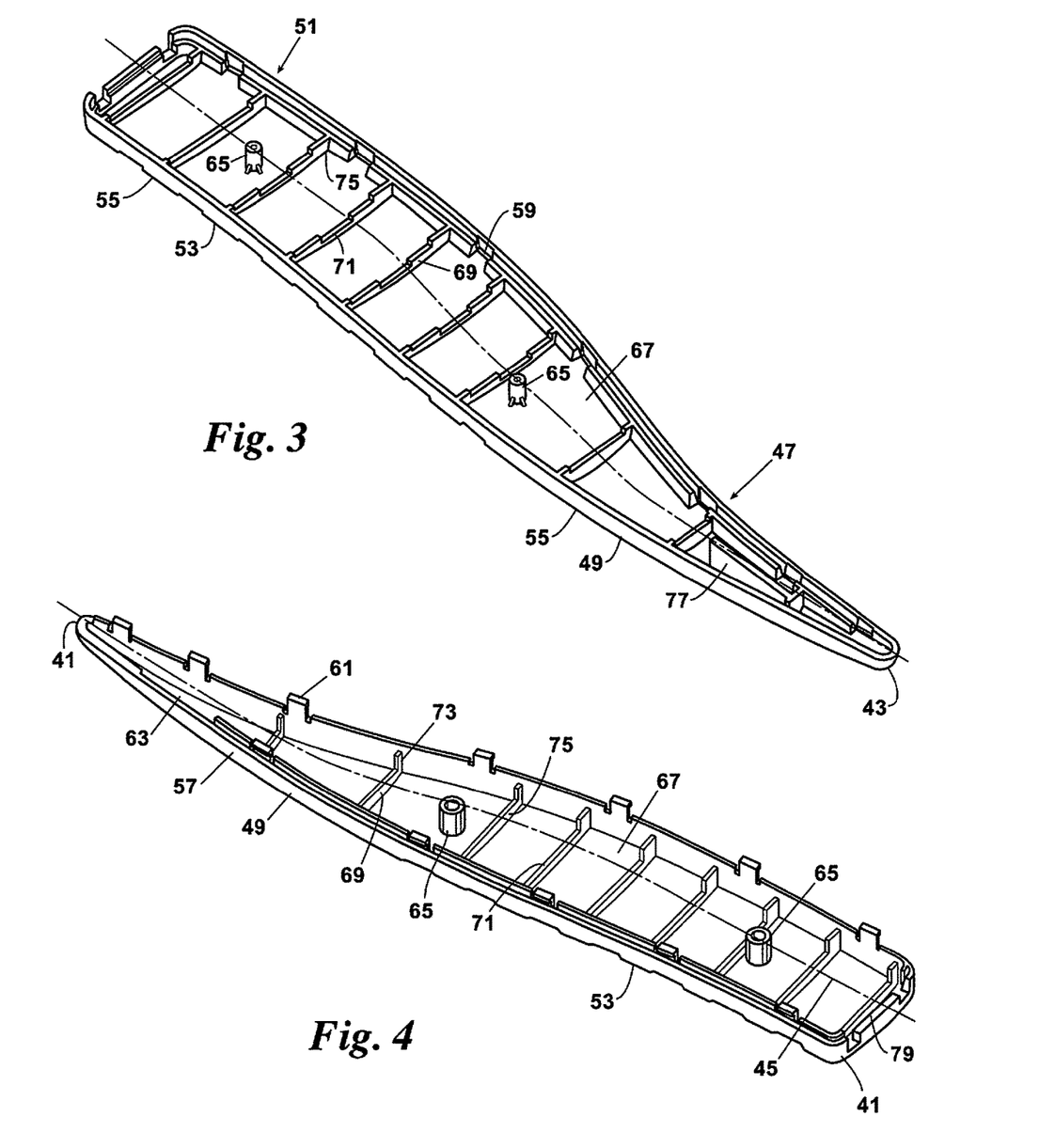
FIG. 3 shows the various elements of the front (first) housing component.
FIG. 4 shows the various elements of the rear (second) housing component
Figures 5, 9:
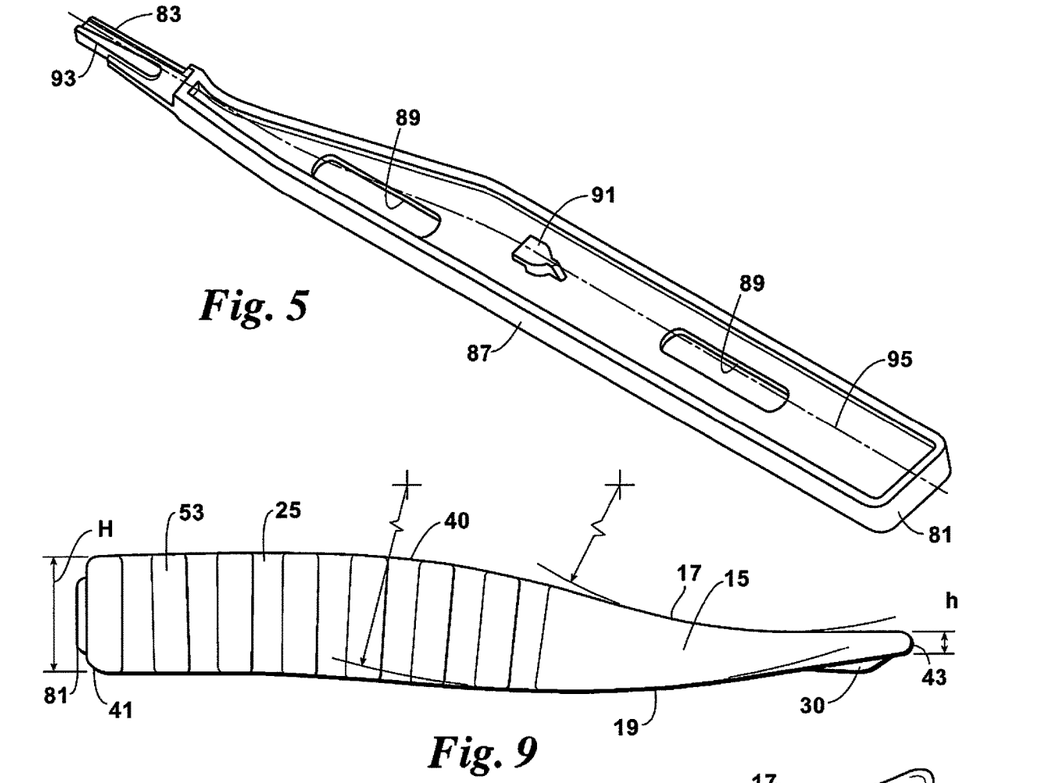
FIG. 5 shows the various elements of the plunger component.
FIG. 9 is a front elevation view of an embodiment of the device.
Figures 6, 7, 8:
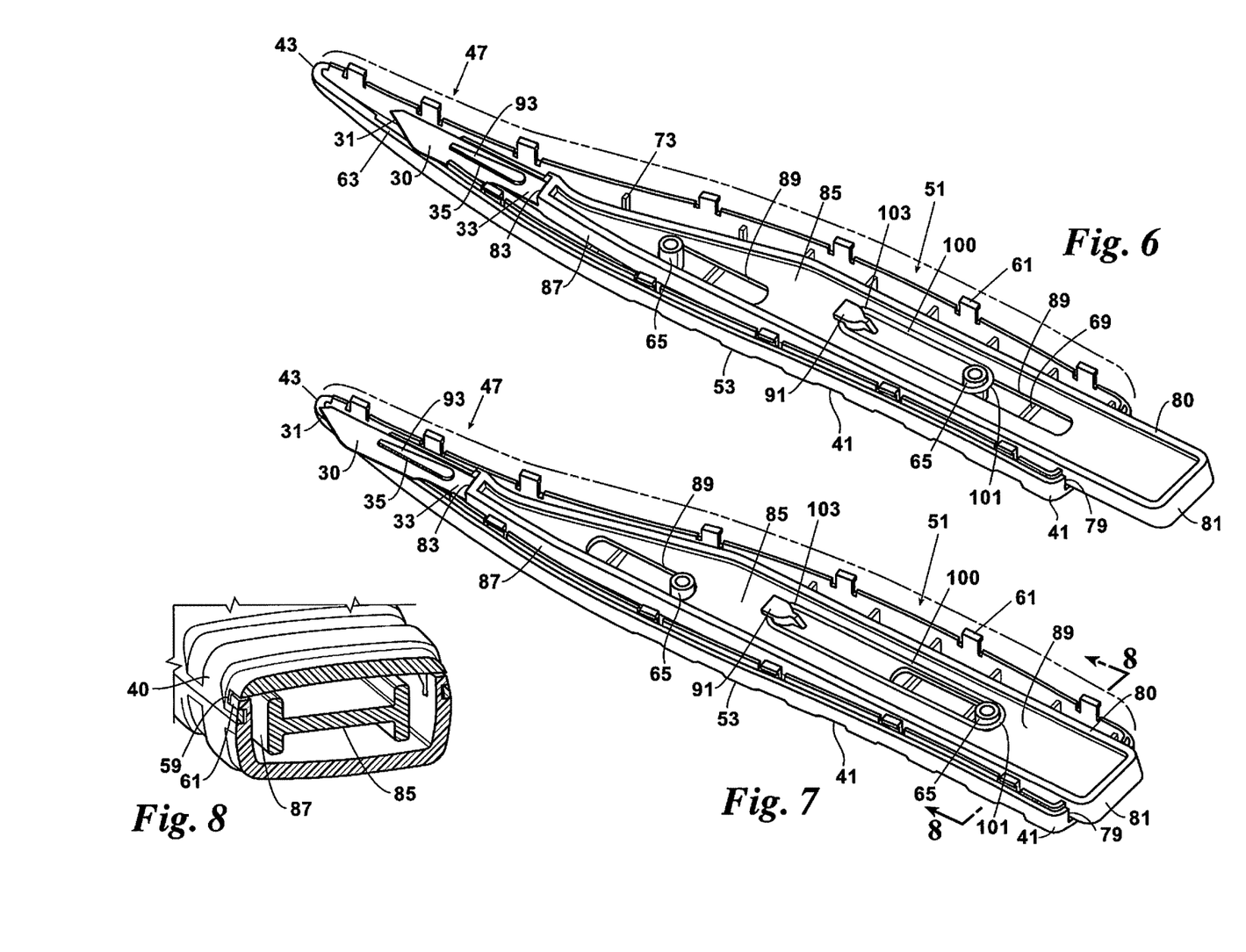
FIG. 6 shows all components in the assembled state with blade retracted.
FIG. 7 shows all components in the assembled state with the blade extended.
FIG. 8 shows a cross section of housing retention snap tabs and openings in assembled state, taken along section line 8-8 of FIG. 7.
Figure 10:
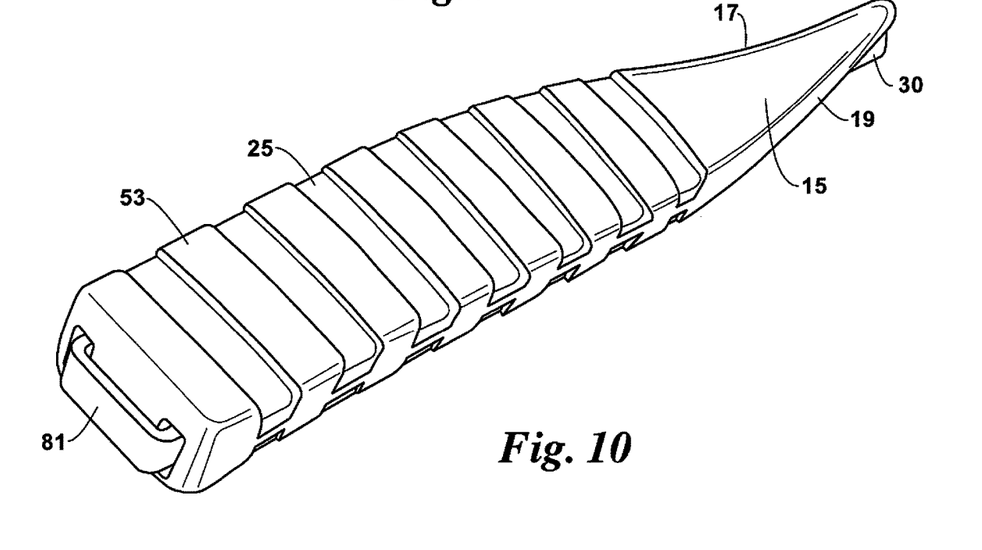
FIG. 10 is an isometric view.
Figure 11:
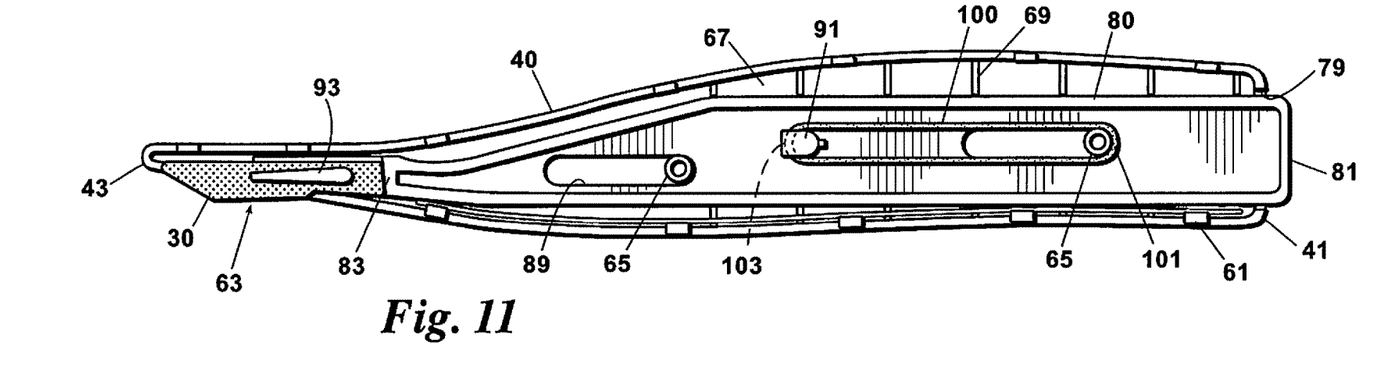
FIG. 11 is a cross-section view.
Figures 12, 13:
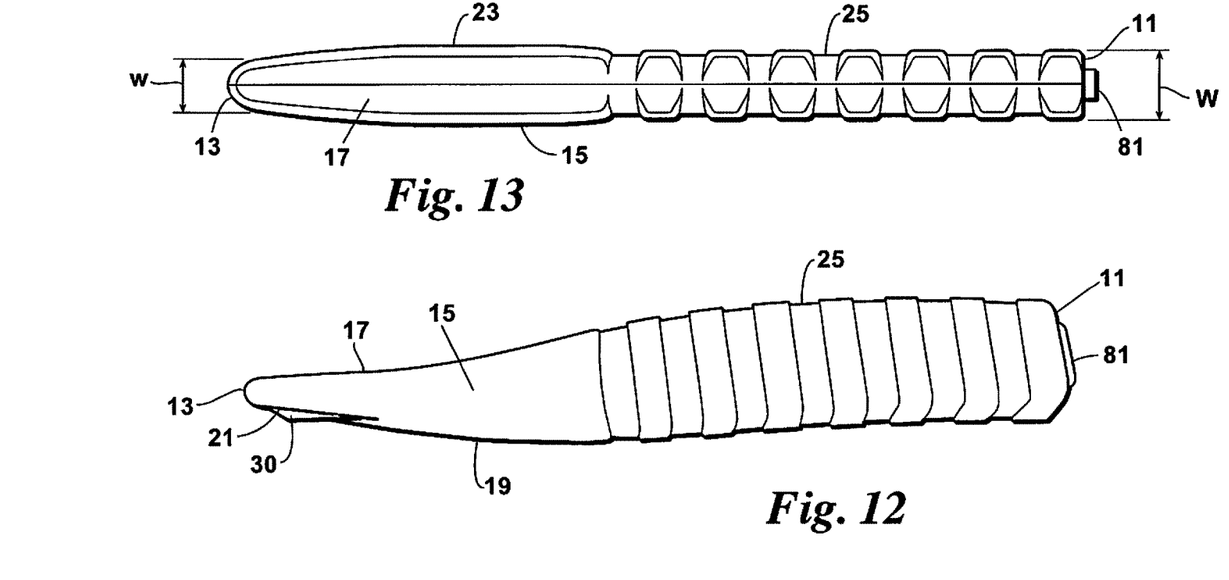
FIG. 12 is an isometric view.
FIG. 13 is a top plan view.

10 Incising tool
11 Proximal (actuator) end
13 Distal (insertion) end
15 Curved section
17 Top wall surface
20 Bottom wall surface
21 Blade expressing aperture
23 Ellipsis- or oval-shaped periphery
25 Handle section
30 Surgical cutting blade
31 Proximal end
33 Distal end
35 Mounting slot
40 Housing
41 Proximal (actuator) end
43 Distal (insertion) end
45 Central longitudinal centerline
47 Sloping or curved section
49 Exterior wall surface
51 Handle section
53 Annular rib
55 Front (first) housing half
57 Rear (second) housing half
59 Snap connector receiver
61 Snap connector
63 Blade expressing aperture
65 Alignment pin
67 Inner wall surface
69 Stiffening rib
71 Channel
73 Flange
75 End
77 Plunger stop
79 Plunger clearance opening
80 Plunger
81 Proximal (exposed actuator) end
83 Distal (blade) end
85 Web
87 Flange
89 Alignment slot
91 Retention pin
93 Blade mounting post
95 Central longitudinal centerline
100 Elastomer band
101 Housing-retained end
103 Plunger-retained end
H Height at proximal end
h Height at distal end
W Width at proximal end
w Width at distal end

DETAILED DESCRIPTION

Referring to the drawing figures, embodiments of an incising tool 10 of this disclosure create an incision, or incisions, for purposes of relieving obstruction in the birth canal during child birth. The tool 10 provides a unique contour that narrows in height in a longitudinal direction toward a distal (insertion tip) end 13 of the tool from its proximal (actuator) end 11 and widens in a lateral (widthwise) direction from the distal end 13 toward the proximal end 11. The distal end 13 may form a curved end or insertion tip. The narrowing in height toward the distal end 13 provides a curved section 15 of the tool 10 that helps "shoe horn" the tool 10 into proper placement between the vaginal wall and the baby's head. The curved section 15 also helps reduce localized stress caused by insertion of the tool 10. The curved section 15 may have a duckbill shape.

In embodiments, the curved section 15 may flatten out into a top wall surface 17 that is located opposite a bottom wall surface 19 containing a blade expressing aperture 21. In some embodiments, the top wall surface 17 may include an ellipsis- or oval-shaped periphery 23. The bottom wall surface 19 may include a curved or angled surface, correlating to the top wall surface 17. The top wall surface 17, as well as the bottom wall surface 19, may include a slight crown or draft angle. In embodiments, the draft angle may be in a range of 0.5° to 3°, there being discrete values and subranges within this broader range. For the purposes of this disclosure, a top wall surface 17 having this amount draft is still considered flat. By way of a non-limiting example, the draft may be 1°±industry standard tolerance.

As a surgical cutting blade 30 is expressed from the aperture 21, the baby's head is protected from the nowexposed blade 30. The width "w" of the tip 13 is sized for insertion and such that the baby's head applies sufficient downward pressure on the blade 30 for a proper depth of incision without exceeding an amount of pressure that may bruise or otherwise injure the opposing portion of the baby's head in contact with the tip 13. A handle section 25 of the tool 10 provides a gripping surface for the user to hold onto the tool 10 as well as actuating means for expressing the blade 30. The handle section 25 may include a curvature.

In embodiments, the tool 10 includes a housing 40 that provides the contour and entirely contains the blade 30 until expressed by the user, the blade 30 automatically retracting into the housing 40 after use so that the tool 10 may be removed from the canal. The blade 30 may be a #10 steel scalpel blade. In embodiments of the housing 40, the housing 40 contains actuating means in the form of a sliding plunger 80, biasing means in the form of an elastomeric band 100 to hold the plunger 80 in a fully retracted position, and a surgical cutting blade 30, mounted on the plunger 80 for extension out of, and retraction into, the housing 40. The blade 30 is expressed by applying an axial force to an actuator end 81 of the plunger 80 that passes through an opening 79 located at a proximal (actuator) end 41 of the housing 40. Once this force is removed, the blade 30 automatically retracts into the housing 40 as the plunger 80 moves away from a distal (insertion) end 43 of the housing 40 and toward the actuator end 41.

As previously discussed in reference to the tool 10, the housing 40 narrows in height (z-axis or height-wise direction) along its central longitudinal centerline 45 (x-axis or lengthwise direction), the height "h" being less at the distal end 43 of the housing 40 than the height "H" at a proximal end 41. In embodiments, the height h is selected to be as short as possible yet still completely shroud the blade 30 when the blade 30 is fully retracted into the housing 40. A sloping or curved section 47 of the housing 40 contains smooth exterior wall surfaces 49 as opposed to those of a handle section 51 which contains a plurality of spaced-apart annular ribs 53. Curved section 47 has a width "W" toward the proximal end 41 and narrows to a width "w" at the distal end 43. In embodiments, the curved section 47 provides a duckbill shape. The ribs 53 of the handle 51 provide gripping surfaces for the user's hand. Other types of gripping or textured surfaces may be used. The handle section 51 may be straight or include a curved profile.

In embodiments, the housing 40 may be a two-part, molded plastic housing comprised of a front (first) housing half 55 and rear (second) housing half 57. The two halves 55, 57 may be complementary shaped and connected to one another using snap connection means. For example, one half 55 may include snap tab openings or slots 59 and the other half 57 may include corresponding snap tabs 61 (or vice versa). When in an assembled state, the halves 55, 57 provide the plunger clearance opening 79 located at the proximal end 41 of the housing 40 as well as a blade expressing aperture 63 located toward the distal end 43.

The connection means may also include a pair of alignment pins 65 located on an inner wall surface 67 of each half 55, 57. The alignment pins 65 extend, like the tabs 61 do, in a transverse direction (Y-axis or widthwise direction) to that of the central longitudinal centerline 45. The alignment pins 65—which may be configured as male on one half 55 or 57 and female on the other half 57 or 55—help with assembly and align and guide the plunger 80. At least one of the alignment pins 65 may function as a retention pin for one end 101 an elastomer band 100. The other end 103 of the band 100 may be connected to a retention pin 91 of the plunger 80.

To help with structural integrity of the housing 40, a plurality of stiffening ribs 69 may be placed along the inner wall surface 67 of each half 55, 57. The ribs 69 may also be configured to function as guides for the sliding plunger 80. In some embodiments, one or more of the ribs 69 may include a guide channel 71, a flange 73 at one or both ends 75 of the ribs 69, or a combination of the guide channel 71 and flange 73. Additionally, a blade safety back up/hard plunger stop 77 may also be located toward the distal end 43 along the inner wall surface 67 of at least one of the halves 55, 57.

In embodiments, the sliding plunger 80 may be a molded plastic plunger shaped complementary to that of the housing 40, narrowing in height toward its distal end 83 from its proximal end 81. The proximal end 81, which functions as an actuating end, may be shaped complementary to that of the opening 79 at the proximal end 41 of the housing 40. For example, the end 81 and opening 79 may be square- or rectangular-shaped. The distal end 83 may function as a stop against which a proximal end 31 of the surgical cutting blade 30 rests. A mounting post 93, shaped complementary to that of a mounting slot or opening 35 of the blade 30, may be located toward the distal end 81. The plunger 80 may an I-beam shaped plunger in cross-section, for example, forming a web 85 and a flanged perimeter 87, the perimeter 87 having greater height than the web 85. When the plunger 80 is placed in the housing half 55, 57, the flanged perimeter 87 lies opposite the flanged portion 73 of the stiffening ribs 69. The plunger opening 79 may be shaped complementary to that of the I-beam shaped plunger 80, thereby providing a guide channel.

To permit movement between the retracted and extended positions, the plunger 80 may include a pair of slots 89 configured to receive the alignment pins 65 of the housing 40. A length of each slot 89 is greater than that of a diameter of a respective alignment pin 65, the length determining an overall axial travel distance of the plunger 80. The plunger 80 may also include a retention pin 91, configured to retain one end 103 of the elastomer band 100. The pin 91 may be located between the pair of slots 89.

The blade 30 may be extended from the housing 40 by use of the operator's thumb to depress the actuator end 81 of the plunger 80, thereby expressing the blade 30 through the aperture 63 formed by the two halves 55, 57 of the housing 40. Once fully extended, the exposed blade 30 is held in a static position by way of the operator's thumb depressed against the plunger 80. To retract the blade 30, the operator simply relaxes the pressure of their thumb on the plunger 80 or removes their thumb completely from contact with the plunger 80. The biasing means are immediately responsive to this relaxation or removal of pressure, pulling the plunger 80 and attached blade 30 towards the proximal end 41 of the housing 40.

Embodiments of an incising tool of this disclosure allow for the introduction of the cutting blade into the vagina and into the location of muscular obstruction without cutting the mother or child. The unique contours of the housing, which may include a duckbill shape, provide an effective way to shoe-horn the tool and its cutting blade into a precise location between the baby's head and mother's pelvic floor muscles. This area will be under heavy tension due to the muscles stretching and the pressure of the baby passing through the birth canal. Upon introduction into the location between the child's crowning head and the muscular ring holding the child from exiting the womb, the scalpel blade may be extended as described above to create an incision into the tissue and muscle of the pelvic floor. The pressure of the child's crowning head on the back of the non-cutting top wall surface of the tool's housing, combined with the cutting motion provided by the operator parallel to the blade's cutting edge, drives the scalpel blade to the required depth to relieve the tension causing obstruction.

Once the obstruction has been relieved due to the precisely located incision, the operator's thumb can be relaxed against the plunger or removed from contact with the plunger completely and the blade will be quickly retracted and the tool can be removed from the vaginal canal without make any additional incisions. No anterior incisions are made outside of the vaginal canal and those that are made are made posteriorly in the vaginal canal and minimal in depth.

While embodiments of the incising tool have been described in detail, modifications to its construction and use may be made without departing from the scope of the following claims. The claims encompass the full range of equivalents to which the recited elements are entitled.

The invention claimed is:

1. A pelvic floor muscle incising tool comprising:
   a surgical blade;
   a housing including an insertion end, an actuator end, and an exterior wall surface located between the ends, the housing narrowing in height toward the insertion end from the actuator end, a portion of the exterior wall surface located toward the actuator end including a plurality of spaced-apart annular ribs, another portion of the exterior wall surface located toward the insertion end including a curved section narrowing in width toward the insertion end and including a flat upper wall surface and a curved lower wall surface located opposite the flat wall surface, the curved lower wall surface including a blade opening contained between the insertion and actuator ends, each said upper and lower wall surfaces ending at the insertion end, the housing further containing a pair of alignment pins arranged transverse to a central longitudinal centerline of the housing; and a plunger housed by the housing and including a proximal end, a distal end, and a mount configured to retain the surgical blade located on the distal end, the proximal end of the plunger extending outward past the actuator end of the housing when in a fully retracted position, the plunger further including a retention pin and a pair alignment slots arranged parallel to the central longitudinal centerline of the housing and extending lengthwise, each of the alignment slots containing a respective alignment pin of the pair of alignment pins, the retention pin arranged transverse to a central longitudinal centerline of the plunger and coaxially aligned with one of the alignment slots, wherein when the plunger moves to a fully actuated position, the surgical blade is in an expressed state below the curved lower wall surface and the housing, wherein in the expressed state the surgical blade is proud of all surfaces of the curved lower wall surface extending from the blade opening, a distal end of the surgical blade being rearward of the insertion end of the housing.

2. The incising tool of claim 1, further comprising biasing means configured to urge the plunger toward the actuator end of the housing.

3. The incising tool of claim 2, the biasing means including an elastomeric band, one end of the elastomeric band retained by the retention pin and another end of the elastomeric band retained by one of the alignment pins.

4. The incising tool of claim 1, wherein the plunger narrows in height from its proximal end to its distal end.

5. The incising tool of claim 1, wherein the housing is a two-part housing comprising complementary shaped first and second halves.

6. The incising tool of claim 5, further comprising the first half including a plurality of snap connectors and the second half including a plurality of snap connector receivers.

7. The incising tool of claim 1, further comprising the plunger being I-shaped in cross section.

8. The incising tool of claim 7, the plunger including a central web with a flange located about a periphery of the web.

9. The incising tool of claim 1, further comprising the housing including a plurality of plunger guides located along an inner wall surface of the housing.

10. The incising tool of claim 1, further comprising the housing including an inner wall surface including a plurality of spaced-apart ribs.

11. A pelvic floor muscle incising tool comprising:
a surgical cutting blade;
a housing including an insertion end, an actuator end, and an exterior wall surface located between the ends, the housing narrowing in height toward the insertion end from the actuator end and forming a curved section toward the insertion end, a portion of the exterior wall surface of the curved section narrowing in width toward the insertion end and including a flat upper wall surface and a curved lower wall surface including a surgical cutting blade opening located opposite the flat upper wall surface, the curved lower wall surface being a pelvic floor muscle facing surface, said flat upper wall surface and said curved lower wall surface ending at the insertion end;
a plunger housed by the housing and including a proximal end, a distal end, and a mount configured to retain the surgical cutting blade located on the distal end, proximal end of the plunger extending outward past the actuator end of the housing when in a fully retracted position;
wherein when the plunger moves to a fully actuated position, the surgical cutting blade is in an expressed state below the curved wall surface and the housing, wherein in the expressed state the surgical blade is proud of all surfaces of the curved lower wall surface extending from the surgical cutting blade opening, a distal end of the surgical cutting blade being rearward of the insertion end of the housing; and wherein the flat upper wall surface shields an entire length of the surgical cutting blade when in the expressed state.

12. The incising tool of claim 11, further comprising another portion of the exterior wall surface located toward the actuator end including a plurality of spaced-apart annular ribs.

13. The incising tool of claim 12, further comprising the housing containing a pair of alignment pins arranged transverse to a central longitudinal centerline of the housing.

14. The incising tool of claim 13, further comprising the plunger including a retention pin and a pair alignment slots arranged parallel to the central longitudinal centerline of the housing and extending lengthwise, each alignment slot of the pair of alignment slots containing a respective alignment pin of the pair of alignment pins, the retention pin arranged transverse to a central longitudinal centerline of the plunger and coaxially aligned with one of the alignment slots.

15. The incising tool of claim 14, further comprising an elastomeric band including one end retained by the retention pin and another end retained by one of the alignment pins.

16. The incising tool of claim 11, wherein the plunger narrows in height from its proximal to its distal end.

17. The incising tool of claim 11, wherein the housing is a two-part housing comprising complementary shaped first and second halves, the halves connectable to one another.

18. A pelvic floor muscle incising tool comprising:
a surgical blade;
a housing including an insertion end, an actuator end, and a curved section toward the insertion end;
the curved section including an upper wall surface and a lower wall surface located opposite the upper wall surface, each said wall surface ending at the insertion end, the lower wall surface being a pelvic floor muscle facing surface and including a blade opening rearward of the insertion end;
a plunger received by the housing and including a mount configured to retain a surgical blade;
wherein when the plunger moves to a fully actuated position, the surgical blade is in an expressed state below the lower wall surface and the housing, wherein in the expressed state the surgical blade is proud of all surfaces of the curved lower wall surface extending from the surgical cutting blade opening, a distal end of the surgical blade being rearward of the insertion end.

19. The incising tool of claim 18, wherein the upper wall surface shields an entire length of the surgical blade when in the expressed state.

\* \* \* \* \*